United States Patent
Junino et al.

Patent Number: 5,730,962
Date of Patent: Mar. 24, 1998

[54] DEPIGMENTING COSMETIC OR DERMATOLOGIC COMPOSITION CONTAINING A BENZOFURAN DERIVATIVE AND ITS USE IN DEPIGMENTATING SKIN

[75] Inventors: Alex Junino, Livry Gargan; Quang Lan N'Guyen, Antony; Remy Tuloup, Miniac Sous Becherel; Christian Blaise, Sevran, all of France

[73] Assignee: L'Oreal, Paris, France

[21] Appl. No.: 914,150

[22] Filed: Jul. 16, 1992

[30] Foreign Application Priority Data

Jul. 17, 1991 [FR] France .................. 91 09028

[51] Int. Cl.$^6$ .................. A61K 7/48; A61K 7/00
[52] U.S. Cl. .................. 424/62; 424/401
[58] Field of Search .................. 424/401, 63, 59, 424/62; 549/462

[56] References Cited

U.S. PATENT DOCUMENTS

| | | | |
|---|---|---|---|
| 2,320,746 | 6/1943 | Paul | 549/462 |
| 4,098,882 | 7/1978 | Lang | 514/972 |
| 4,639,536 | 1/1987 | Fellows | 549/462 |
| 4,857,516 | 8/1989 | Terao | 549/462 |
| 4,966,907 | 10/1990 | Caldwell | 514/337 |
| 5,043,354 | 8/1991 | Tsujii | 514/469 |

FOREIGN PATENT DOCUMENTS

| | | |
|---|---|---|
| 2285854 | 4/1976 | France . |
| 2221680 | 2/1990 | United Kingdom . |

*Primary Examiner*—Sally Gardner-Lane
*Attorney, Agent, or Firm*—Nixon & Vanderhye P.C.

[57] ABSTRACT

A depigmenting cosmetic or dermatologic composition for use in bleaching the skin or treating pigmental spots contains in a vehicle suitable for topical application to the skin a benzofuran derivative having the formula

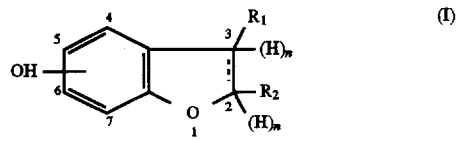

wherein the OH function occupies position 5 or 6, $R_1$ and $R_2$, each independently, represent hydrogen or alkyl having 1–4 carbon atoms, n is 0 or 1, when n is 0, the $C_2$–$C_3$ bond is a double bond, and when n is 1, the $C_2$–$C_3$ bond is a single bond.

7 Claims, No Drawings

DEPIGMENTING COSMETIC OR DERMATOLOGIC COMPOSITION CONTAINING A BENZOFURAN DERIVATIVE AND ITS USE IN DEPIGMENTATING SKIN

The present invention relates to a cosmetic or dermatologic composition in a cosmetically or dermatologically acceptable medium suitable for topical application to the skin, a benzofuran derivative in an amount effective to bleach the skin or to treat pigmentary spots thereon.

It is known that the formation mechanism of skin pigmentation, that is, the formation of melanins is particularly complex and schematically involves the following principal steps:

Tyrosine→Dopa→Dopaquinone→Dopachrome→Melanins, the enzyme intervening in this reaction scheme being, essentially, tyrosinase.

The substances most employed, presently, as depigmentation agents are, more particularly, hydroquinone and its derivatives, in particular, its ethers such as the monomethyl ether of hydroquinone and arbutin.

These compounds, if they have a certain effectiveness, are unfortunately not free from side effects, which renders their use weak approaching dangerous.

Thus, hydroquinone, the use of which is moreover limited to a concentration of 2 percent, is a compound particularly irritating and cytotoxic to the melanocyte. Its replacement, total or partial, has been envisaged by numerous authorities.

There has been proposed, in U.S. Pat. No. 4,526,179 certain fatty esters of hydroquinone having good activity and being less irritating and more stable than hydroquinone.

Other hydroquinone derivatives have also been proposed in Japanese application, No. 27909/86 which do not exhibit the disadvantages of hydroquinone but whose effectiveness has been determined to be relatively mediocre.

It is well established that a substance exerts a depigmenting activity if it acts directly on the vitality of the epidermic melanocytes where melanogenesis evolves normally, and/or if it interferes with one of the steps in the biosynthesis of melanins or by inhibiting one of the involved enzymes or by being itself interposed as a structural analogue in the synthesis process which can thus be blocked from the depigmenting effect.

The use of topical depigmenting substances exhibiting good effectiveness and being harmless, is quite particularly desired so as to treat regional hyperpigmentations by melanocytal hyperactivity such as idiopathic melasmas, occurring during pregnancy ("mask of pregnancy" or chloasma) or subsequent to estro-progestative contraception, localized hyperpigmentations by hyperactivity and benign melanocytal proliferation such as senile pigmental spots, called actinic lentigo, casual hyperpigmentations such as photosensibilization and post-lesional cicatrization, as well as certain leucodermies such as vitiligo where, in the absence of the power to repigment injured skin, depigmentation is achieved on the areas of residual normal skin so as to give to the whole of the skin a homogenous white shade or color.

After numerous studies on various substances it has now been noted in a quite surprising manner that certain benzofuran derivatives have a particularly pronounced depigmenting activity, very good skin tolerance and a melanogenesis inhibiting activity of 1.5 to 2 times greater than that of hydroquinone.

The present invention thus relates to a cosmetic or dermatologic composition having a depigmenting activity comprising in a cosmetically or dermatologically acceptable medium a benzofuran derivative having the formula

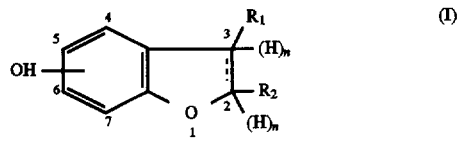

wherein
the OH function occupies position 5 or 6,
$R_1$ and $R_2$, each independently, represent hydrogen or alkyl having 1–4 carbon atoms,
n is 0 or 1,
when n is 0, the $C_2$-$C_3$ bond is a double bond, and
when n is 1, the $C_2$-$C_3$ bond is a single bond.
Representative compounds of formula (I) include
5-hydroxybenzofuran,
6-hydroxybenzofuran,
2,3-dihydro-6-hydroxybenzofuran,
3-methyl-6-hydroxybenzofuran,
2,3-dimethyl-6-hydroxybenzofuran,
2,3-dihydro-3-methyl-6-hydroxybenzofuran and
2-methyl-5-hydroxybenzofuran.

The benzofuran derivatives are known and have been described in the literature and principally in the René and Royer article, Bull. Soc. Chim. Fr., 1973, 2355–2356 and the Oberholzer et al article, J. C. S. Perkin I, 1977, 423–426.

In the depigmenting compositions in accordance with the invention the concentration of the benzofuran derivatives of formula I generally ranges from 0.01 to 10 percent and preferably from 0.5 or 5 percent by weight based on the total weight of the composition.

The cosmetically or dermatologically acceptable vehicle or medium can be, principally, an aqueous or hydroalcoholic solution, an emulsion of the oil-in-water or water-in-oil type, an emulsified gel or even a hipbase system.

Preferably, the compositions according to the invention are provided in the form of a lotion, a cream, a milk, a gel, a mask, microspheres or nanospheres, or vesicular dispersions. In the case of vesicular dispersions, the lipids constituting the vesicles can be of the ionic or nonionic type or even a mixture of them.

These cosmetic compositions can also contain a humectant, a surface active agent, a keratolytic agent, an anti-inflammatory agent, a complexing agent, an antioxidant, a preservative, a perfume or a sunscreen agent.

The compositions are applied topically in an amount corresponding to application dosages which are conventional for this type of composition under consideration (gel, cream, lotion, etc . . . ). For example, in the case of a cream, from 0.5 to 3 mg and principally from 1 to 2 mg of cream per 1 $cm^3$ of skin are employed at an application rate of one or two applications per day.

"In Vitro" Studies

Certain ones of the benzofuran derivatives have been comparatively studied with respect to hydroquinone, at molar equivalent amounts, in the in vitro inhibition test of the activity of tyrosinase.

According to this test the amount of dopachrome formed during the course of the reaction chain for the transformation of tyrosine into melanins is followed by visible spectrometry at 475 nm. These reactions are catalyzed, in vitro, by fungus tyrosinase, in the presence of a reducing co-substrate (for example, L-dopa in a small amount) to initiate the hydroxylation reaction of L-tyrosine into L-dopa, which is then catalytically oxidized into dopaquinone, then into dopachrome, produced intermediate before the non-enzymatic oxidation reactions terminating in the formation of melanins.

The concentration of dopachrome formed during the course of time in the presence and in the absence of the inhibitor is then measured.

The concentrations of inhibitors are fixed at 50 molar percent relative to the tyrosine concentration in the reaction medium.

The inhibition effect is expressed by the reduction of the maximum amount of dopachrome formed (optical density value at 475 nm read at the plateau of the curve) relative to the amount obtained in the absence of inhibitor.

Experimental Protocol

Reactants:

A—0.1M phosphate buffer pH=6.5 (TWEEN 20 at 1%)
B—L-tyrosine mother solution at $2 \times 10^{-3}$M in A
C—L-dopa mother solution at $10^{-4}$M in A
D—Fungus tyrosinase mother solution at 2,400 units/ml in A
E—Inhibitor mother solution at $10^{-2}$M in A (solutions C and D are prepared the same day).

Results

Control cell: 3 ml of A
Test cell: 1 ml of B
0.1 ml of C
1.85 ml of A+E
Homogenize and equilibrate at 25° C.
add 0.05 ml of D
rapidly mix and observe the kinetics by the measurement of the absorbance at 475 nm as a function of time.

TABLE I

| Compound | % inhibitor |
|---|---|
| 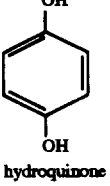<br>hydroquinone | 33% |
| 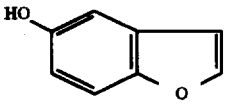<br>5-hydroxybenzofuran | 56% |
| 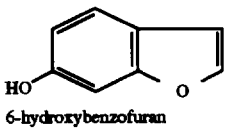<br>6-hydroxybenzofuran | 54% |
| 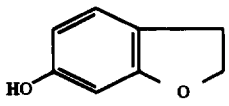<br>2,3-dihydro-6-hydroxybenzofuran | 66% |

As can be seen the benzofuran derivatives of the compositions according to the invention have a melanogenesis inhibiting activity greater than that of hydroquinone.

EXAMPLE OF PREPARATION

Preparation of 6-hydroxybenzofuran

In a reactor equipped with a condenser, a thermometer, an addition ampoule, a nitrogen lead in tube and a mechanical stirrer/heating system, there are introduced 600 cm³ of tetrahydrofuran (THF).

After degassing with nitrogen, there are added in small amounts 14 g of LiAlH$_4$ over a 30 minute period. At the end of the addition the reaction mixture is heated to 67° C. At this temperature there is added, over a 2 hour period, a solution of 50 g of 6-hydroxy-3-coumaranone dissolved in 1.4 liters of boiling THF.

At the end of the addition, the reaction mixture is cooled to 30° C. and then poured into 2 liters of a 2N HCl solution which is vigorously stirred for a period of 30 minutes.

After extraction three times with 300 cm³ of ethyl ether and washing the organic phase twice with 200 cm³ of water, the product is dried on magnesium sulfate, filtered and then evaporated to dryness. 50 g of the crude product in oily form are obtained.

The crude product is then purified by chromatography on a silica column eluted with dichloromethane. 25 g of the expected product in oily form are obtained. Yield=50

EXAMPLES OF COMPOSITIONS

Example 1—Depigmenting Lotion

| | |
|---|---|
| Ethyl alcohol, 96% | 47.8 g |
| Polyethylene glycol oxyethylenated with 8 moles of ethylene oxide | 28.7 g |
| Ethyl diglycol | 9.5 g |
| Trihydrated sodium acetate | 0.06 g |
| Acetic acid | 0.03 g |
| N-octanoyl-5 salicylic acid | 2.0 g |
| 6-hydroxybenzofuran | 2.5 g |
| Water, sufficient amount for | 100.00 g |

In this example, the 6-hydroxybenzofuran can be replaced by the same amount of 2,3-dimethyl-6-hydroxybenzofuran or 2,3-dihydro-3-methyl-6-hydroxybenzofuran.

Example 2—Oil-in-water Emulsion

| | |
|---|---|
| Ceteareth 20 (polyoxyethylenated cetyl stearyl alcohol) | 1.0 g |
| Ethylene glycol palmitostearate | 3.0 g |
| Cococaprylate/caprate (esters of $C_8$–$C_{10}$ acids and $C_{12}$–$C_{18}$ fatty alcohols) | 5.0 g |
| Carboxyvinyl polymer sold under the trade name "CARBOMER 934" by Goodrich | 0.3 g |
| Triethanolamine | 0.9 g |
| Ethyl alcohol, 96% | 20.4 g |
| 6-hydroxybenzofuran | 1.5 g |
| Glycerine | 3.0 g |
| Preservatives | 0.2 g |
| Perfume | 0.1 g |
| Water, sufficient amount for | 100.0 g |

In this example, the 6-hydroxybenzofuran can be replaced by the same amount of 5-hydroxybenzofuran or 3-methyl-6-hydroxybenzofuran.

Example 3—Water-in-oil Emulsion

| | |
|---|---|
| Propyleneglcyol | 10.0 g |
| 6-hydroxybenzofuran | 2.0 g |
| Petrolatum oil | 20.0 g |
| Mixture of polycetyldimethylsiloxane oxyethylenated oxypropylenated/polyglyceryl isostearate having 4 moles of glycerol/hexyl laurate | 3.0 g |
| Preservatives | 0.2 g |
| Perfume | 0.1 g |
| Water, sufficient amount for | 100.0 g |

In this example, the 6-hydroxybenzofuran can be replaced by the same amount of 2,3-dihydro-3-methyl-6-hydroxybenzofuran.

Example 4—Water-in-oil Emulsion

| | |
|---|---|
| Propylene glycol | 10.0 g |
| 6-hydroxybenzofuran | 5.0 g |
| Petrolatum oil | 20.5 g |
| Esters of fatty acid and sorbitol | 5.0 g |
| Hectorite modified by stearyl dimethylbenzylammonium chloride in glyceryl dicaprate | 5.0 g |
| Cococaprylate/caprate (esters of $C_8$-$C_{10}$ acids and $C_{12}$-$C_{18}$ fatty alcohols) | 1.0 g |
| Preservatives | 0.2 g |
| Perfume | 0.1 g |
| Water, sufficient amount for | 100.0 g |

In this example the 6-hydroxybenzofuran can be replaced by the same amount of 3-methyl-6-hydroxybenzofuran.

We claim:

1. A depigmenting cosmetic or dermatological composition for topical application to skin comprising in a cosmetically or dermatologically acceptable vehicle an effective amount of a depigmenting substance consisting essentially of a benzofuran derivative having the formula:

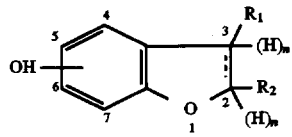

wherein the OH function is in the 5 or 6 position, $R_1$ and $R_2$, each independently, represent hydrogen or alkyl having 1–4 carbon atoms, n is 0 or 1, when n is 0, the $C_2$-$C_3$ bond is a double bond, and when n is 1, the $C_2$-$C_3$ bond is a single bond.

2. The composition of claim 1 wherein said benzofuran derivative is selected from the group consisting of 5-hydroxybenzofuran, 6-hydroxybenzofuran, 2,3-dihydro-6-hydroxybenzofuran, 3-methyl-6-hydroxybenzofuran, 2,3-dimethyl-6-hydroxybenzofuran, 2,3-dihydro-3-methyl-6-hydroxybenzofuran and 2-methyl-5-hydroxybenzofuran.

3. The composition of claim 1 wherein said benzofuran derivative is present in an amount ranging from 0.01 to 10 percent by weight based on the total weight of said composition.

4. The composition of claim 1 wherein said benzofuran derivative is present in an amount ranging from 0.5 to 5 percent by weight based on the total weight of said composition.

5. The composition of claim 1 in the form of a lotion, a cream, a milk, a gel, a mask, microspheres or nanospheres or a vesicular dispersion.

6. The composition of claim 1 which also includes at least one of a humectant, a surface active agent, a keratolytic agent, an anti-inflammatory agent, a complexing agent, an antioxidant, a preservative, a perfume or a sunscreen agent.

7. A process for depigmenting skin comprising applying to the skin in an amount effective to depigment the skin a depigmenting cosmetic or dermatological composition comprising in a cosmetically or dermatologically acceptable vehicle an effective amount of a depigmenting substance consisting essentially of a benzofuran derivative having the formula

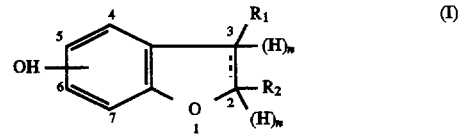

wherein the OH function is in the 5 or 6 position, $R_1$ and $R_2$, each independently, represent hydrogen or alkyl having 1–4 carbon atoms, n is 0 or 1, when n is 0, the $C_2$-$C_3$ bond is a double bond, and when n is 1, the $C_2$-$C_3$ bond is a single bond.

* * * * *